United States Patent [19]

Bachmann et al.

[11] Patent Number: 5,164,365
[45] Date of Patent: Nov. 17, 1992

[54] 1,1,2,3,3,6-HEXAMETHYL-4,5,6,7-TETRAHYDRO-5-INDANONE AND FRAGRANCE COMPOSITIONS CONTAINING SAME

[75] Inventors: Jean-Pierre Bachmann, Wädenswil; Daniel Helmlinger, Gockhausen; Mario Pesaro, Zurich, all of Switzerland

[73] Assignee: Givaudan Corporation, Clifton, N.J.

[21] Appl. No.: 661,361

[22] Filed: Feb. 26, 1991

[30] Foreign Application Priority Data

Mar. 2, 1990 [CH] Switzerland ............. 663/90

[51] Int. Cl.$^5$ ............................................. A61K 7/46
[52] U.S. Cl. ......................................... 512/15; 568/374; 568/819; 568/361
[58] Field of Search ..................... 568/374; 512/15

[56] References Cited

U.S. PATENT DOCUMENTS

| | | | |
|---|---|---|---|
| 3,773,836 | 11/1973 | Hall | 512/15 |
| 3,847,993 | 11/1973 | Hall et al. | 512/15 |
| 3,927,083 | 12/1975 | Hall et al. | 512/15 |

FOREIGN PATENT DOCUMENTS

| | | | |
|---|---|---|---|
| 0115274 | 8/1984 | European Pat. Off. | 512/15 |
| 2330648 | 1/1974 | Fed. Rep. of Germany | 512/15 |
| 2716537 | 11/1977 | Fed. Rep. of Germany | 512/15 |

OTHER PUBLICATIONS

H. Brown, "Hydroboration", W.A. Benjamin Inc., N.Y. 1962 pp. vii–xiii.
D. G. Lee, "Oxidation", R. L. Augustine, editor, Marcel Dekker Inc., N.Y. 1969 pp. 56–81.
R. G. Curtis et al., J. Chem. Soc. (1953) 457.
Org. Syn. Coll. vol. 5, J. Wiley & Sons, N.Y. (1973) 552.
Houben–Weyl, "Methoden der Organischen Chemie" vol. V,Ib (1972) 613.

*Primary Examiner*—James H. Reamer
*Attorney, Agent, or Firm*—Robert F. Tavares; Linda A. Vag

[57] ABSTRACT

The present invention concerns the novel odorant 1,1,2,3,3,6-hexamethyl-4,5,6,7-tetrahydro-5-indanone, I, a process for the manufacture of I, novel intermediates used in the process and fragrance compositions containing I.

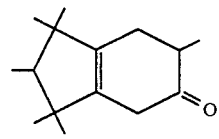

The process for the manufacture of 1,1,2,3,3,6-hexamethyl-4,5,6,7-tetrahydro-5-indanone comprises hydroborating 1,1,2,3,3,6-hexamethyl-4,7-dihydroindane and oxidizing the hydroboration product to 1,1,2,3,3,6-hexamethyl-4,5,6,7-tetrahydro-5-indanone, or reductively alkylating, especially methylating, 5-nitro-1,1,2,3,3,6-hexamethylindane and converting the resulting 5-dialkyl-amino-1,1,2,3,3,6-hexamethylindane into 1,1,2,3,3,6-hexamethyl-4,5,6,7-tetrahydro-5-indanone by reduction of the benzene ring and hydrolysis of the resulting enamine.

2 Claims, No Drawings

1,1,2,3,3,6-HEXAMETHYL-4,5,6,7-TETRAHYDRO-5-INDANONE AND FRAGRANCE COMPOSITIONS CONTAINING SAME

SUMMARY OF THE INVENTION

The present invention concerns the novel odorant 1,1,2,3,3,6-hexamethyl-4,5,6,7-tetrahydro-5-indanone. I, a process for the manufacture of I, novel intermediates used in the process and fragrance compositions containing I.

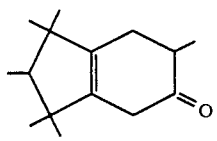

I

Compound I can exist as a mixture of the two possible racemates

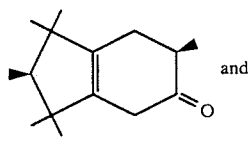

Ia and Ib or as one of these racemates. Formula I is intended to embrace all possible isomers and mixtures thereof.

DESCRIPTION OF THE PREFERRED EMBODIMENTS

Compound I is prepared by a novel process which comprises hydroborating 1,1,2,3,3,6-hexamethyl-4,7-dihydroindane, II, and oxidizing the hydroboration product to the indanone, or reductively alkylating 5-nitro-1,1,2,3,3,6-hexamethylindane, IV, and converting the resulting dialkylamino-indane into the indanone by reduction of the benzene ring and hydrolysis of the resulting enamine. A detailed description of the novel process is provided as follows.

1,1,2,3,3,6-Hexamethyl-4,7-dihydroindane, II, is hydroborated by the addition of borane to the 5,6-double bond of II.

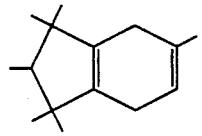

II

The resulting organoborane is then oxidized to the idanone I either directly or via the alcohol intermediate, 1,1,2,3,3,6-hexamethyl- 4,5,6,7-tetrahydro-5-indanol, III.

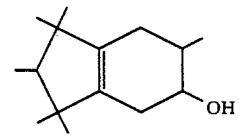

III

Table I hereinafter provides a detailed overview of these two reaction steps as well as a convenient route to the starting material II:

TABLE I

| Process step | Type of reaction | Agent | Solvent | Temperature |
|---|---|---|---|---|
| II → Organoborane | Hydroboration (1) | $B_2H_6$ | Ether, e.g. diethyl ether, tetrahydrofuran, diglyme, etc. | |
| Organoborane → I | Oxidation | $Cr_2O_7^{2-}/H+$ ($H_2SO_4$) | | −20−+30° C., esp. room temperature |
| Organoborane → III | Oxidation | $H_2O_2/OH^-$ (NaOH) | | 0–50° C., esp. 0–25° C. |
| III → I | Oxidation alcohol → ketone (2) | esp. $Cr^{6+}$ — salts e.g. Jones' reagent (4) | Acetone | 0–50° C., esp. 0–25° C. |
| Preparation of II | Reduction (3) | (3) | (3) | (3) |

(1) See e.g. Brown. Hydroboration, W. A. Benjamin Inc. N.Y. 1962; borane solutions in tetrahydrofuran are commercially available, but can also be prepared readily, e.g. by reacting sodium borohydride with boron trifluoride etherate.
(2) See e.g. "Oxidation", Vol. 1, Marcel Bekker Inc. N.Y. (1969) edited by R/L. Augustine, pages 56–81.
(3) Conveniently by reducing 1,1,2,3,3,6-hexamethylindane, see e.g. European Patent Publication No. 115 274 of 8th August 1984.
(4) Conveniently prepared by dissolving chromium trioxide in concentrated sulphuric acid and diluting with water: J. Chem. Soc., 457 (1953).

The benzene derivative, 5-nitro-1,1,2,3,3,6-hexamethylindane, compound IV below, is used as the starting material for the reductive alkylation step.

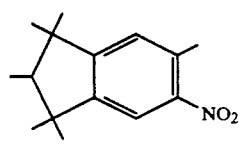

IV

This step is preferably carried out using firstly the system $H_2/Pd/charcoal$ as the reducing agent for the nitro

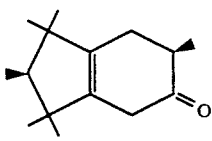

group to the amino group (see Org. Synthesis, Coll. Volume 5, J. Wiley and Sons, N.Y., (1973), 552) and then preferably formaldehyde/H₂/Pd/charcoal as the alkylating, i.e. methylating, agent. Other aldehydes such as acetaldehyde, priopionaldehyde or butyraldehyde may be used as the alkylating agent.

The resulting aniline derivative, 5-dialkylamino-1,1,2,3,3,6-hexamethylindane, preferably the 5-dimethyl derivative, V,

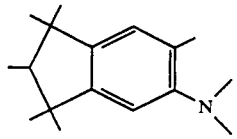

may be effectively reduced in a manner similar to those know per se, e.g. using an alkali metal or alkaline earth metal in liquid ammonia/alcohol according to Birch, or using an alkali metal or alkaline earth metal in an alkylamine/alcohol system according to Benkeser. or electrochemically at metal cathodes (see Houben-Weyl, "Methoden der Organischen Chemie", Volume V Ib (1972) p. 613) followed by hydrolysis of the hydroaromatic enamine, V'.

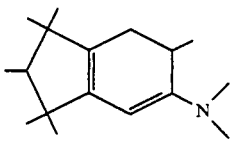

The reduction according to Birch is carried out at a low temperature (e.g. −78° to −33° C.) in liquid ammonia which contains an alcohol such as e g. ethanol. The reduction according to Benkeser is carried out e.g. in methylamine, ethylamine, ethylenediamine etc. in the presence of an alcohol such as ethanol isopropanol, isoamyl alcohol etc. Sodium and lithium are especially suitable metals An addition of diethyl ether or tetrahydrofuran facilitates the dissolution of the aromatic hydrocarbon V.

The hydrolysis of the enamine V', to the indanone I is conveniently carried out using aqueous acid under mild conditions. An inorganic acid or an organic acid can be used as the acid. Examples of such acids are hydrochloric acid, sulphuric acid, oxalic acid, etc. The hydrolysis is preferably carried out at room temperature, although higher temperatures (to about 100° C.) or lower temperatures (to about 0° C.) also come into consideration.

The invention also concerns the use of the compound I, a musk substance, as an odorant. Compound I has powerful, diffuse and very natural-warm notes in the direction of musk, with fruity, sandalwood-like and animalic olfactory aspects.

On the basis of its natural olfactory notes, the compound of formula I is especially suitable for modifying known compositions. In particular its extraordinary olfactory strength is to be emphasised: The oltactory threshold value is 0.67 ng/l; the olfactory value is 123,900. With respect to the definition of olfactory value and olfactory threshold value see e.g. Ulrich A. Huber, Soaps—Oils—Fats—Waxes 110, No. 15 (1984) 448–451. The corresponding values, measured under the same conditions, for the known, structurally similar 6,7-dihydro-1,1,2,3,3-pentamethyl-5(4H)-indanone (1,1,2,3,3-pentamethyl-4,5,6,7-tetrahydro-5indanone; U.S. Pat. No. 3,773,836) are on the other hand 2.5 ng/l and 35,500.

The compound I combines with numerous known odorant ingredients of natural or synthetic origin, whereby the range of the natural odorants can embrace not only readily-volatile but also moderately-volatile and difficultly-volatile components and that of the synthetics can embrace representatives from practically classes of substances as is evident from the following compilation:

Natural products such as tree moss absolute, basil oil, citrus oils (such as bergamot oil, mandarin oil, etc.), mastix absolute, myrtle oil, palmarosa oil, patchouli oil, petitgrain oil Paraguay, wormwood oil, alcohols such as farnesol, geraniol, linalool, nerol, phenylethyl alcohol, rhodinol, cinnamic alcohol, aldehydes such as citral, α-methyl-3 4-methylenedioxyhydrocinnamic aldehyde α-hexylcinnamaldehyde, hydroxycitronellal, Lilial ® (Givaudan) (p-tert.-butyl-α-methyl-dihydrocinnamaldehyde), methylnonylacetaldehyde, ketones such as allylionone, α-ionone, β-ionone, isoraldeine (isomethyl-α-ionone), methylionone, esters such as allyl phenoxyacetate, benzyl salicylate, cinnamyl propionate, citronellyl acetate, citronellyl ethoxolate (citronellyl.O-CO-CO.OC₂H₅), decyl acetate, dimethylbenzylcarbinyl acetate, dimethylbenzylcarbinyl butyrate, ethyl acetoacetate, ethyl aoetylacetate, hexenyl isobutyrate, linalyl acetate, methyl dihydrojasmonate, styrallyl acetate, vetiveryl acetate, lactones such as γ-undecalactone, various components frequently used in perfumery such as musk ketone, indole, p-menthane-8-thiol-3-one, methyleugenol.

Further, the manner in which the compounds round-off and harmonize the olfactory notes of known compositions, but without dominating in an unpleasant manner, is remarkable. Thus, e.g. in perfume bases having tea and green character it underlines the soft and flowery note, and in rose bases the sought-after character of the heavy and sweet Bulgarian rose is underlined.

The compound of formula I (or mixtures thereof) can be used in compositions in wide limits which can range, for example, from 0.1 (detergents)–20% (alcoholic solutions). without these values being, however, limiting values, as the experienced perfumer can achieve effects with even lower concentrations or can synthesize novel complexes with even higher amounts. The preferred concentrations range between about 0.1 and 2%. The compositions manufactured with I can be used for all kinds of perfumed consumer goods (eau de cologne, eau de toilette, extracts, lotions, creams, shampoos, soaps, salves, powders, toothpastes, mouth washes, deodorants, detergents, tobacco etc.).

The compounds I can accordingly be used in the manufacture of compositions and, as will be evident from the above compilation, a wide range of known odorants or odorant mixtures can be used. In the manufacture of such compositions the known odorants referred to above can be used according to methods known to the perfumer such as e.g. from W. A. Poucher, Perfumes, Cosmetics and Soaps 2, 7th Edition, Chapman and Hall, London 1974.

ILLUSTRATION OF THE PREFERRED EMBODIMENTS

EXAMPLE 1

A solution of 201.3 g of a mixture of 60% 1,1,2,3,3,6-hexamethyl-4,7-dihydroindane and 19% 1-ethyl-1,3,3,6-tetramethyl-4,7-dihydroindane in 700 ml of tetrahydrofuran is treated with 21.8 g of finely powdered sodium borohydride. Thereto there is added a solution of 97.4 ml of tetrahydrofuran and the mixture is (about 48% $BF_3$) in 155 ml of tetrahydrofuran and the mixture is stirred at room temperature for 2 hours. At +5° C. there are added dropwise within 15 minutes 130 ml of water, thereupon within 15 minutes 260 ml of 5N NaOH and finally within 45 minutes 260 ml of 30 percent hydrogen peroxide. After stirring at 50° C. for 2 hours the mixture is taken up in hexane and washed neutral with water. After drying the organic phase over $MgSO_4$ and concentrating on a rotary evaporator there remain 215 g of a colourless oil, a mixture of 58% 1,1,2,3,3,6-hexamethyl-4,5,6,7-tetrahydro-5-indanol and 18% 1-ethyl-1,3,3,6-tetramethyl4,5,6,7-tetrahydro-5-indanol. This is dissolved in 1.48 l of acetone; at 0° C. there are added dropwise 365 ml of Jones' reagent in such a manner that the internal temperature does not exceed +6° C. (about 50 minutes). After a further 15 minutes the mixture is taken up in hexane and washed neutral with water; the aqueous phases are extracted with hexane and the organic phase is dried over $MgSO_4$. After concentration there remain 204 g of an oil which are distilled rapidly over a small Vigreux column:

Fractions:

| (1) | 72–80° C./0.2 mbar: | 5.7 g |
|---|---|---|
| (2) | 80–103° C./0.2 mbar: | 164.0 g |
| (3) | Residue: | 31.3 g |

Fraction (2) is finely distilled over a 30 cm Widmer column:

Fractions:

| (1) | 45–62° C./0.05 mbar; $n_D^{20}$ 1.4771–1.4878: | 31.1 g |
|---|---|---|
| (2) | 62–76° C./0.05 mbar; $n_D^{20}$ 1.4878–1.4875: | 28.3 g |
| (3) | 76–83° C./0.05 mbar; $n_D^{20}$ 1.4875–2.4884: | 86.9 g |
| (4) | 83–84° C./0.05 mbar; $n_D^{20}$ 1.4884 and >: | 8.7 g |
|  | Residue: | 7.1 g |

Fraction (3), consisting of 75% 1,1,2,3,3,6-hexamethyl-4,5,6,7-tetrahydro-5-indanone and 25% 1-ethyl-1,3,3,6-tetramethyl-4,5,6,7-tetrahydro-5-indanone, is the so-called olfactory quality; $n_D^{20}=1.4872$.

IR($CHCl_3$): 1705 $cm^{-1}$ $^1$H-NMR (400 MHz, $CDCl_3$) δ(ppm) 0.77(t); 0.83 (s); 0.89 (s); 0.90 (s); 0.90 (d, J=7 Mz); 0.93 (s); 0.94 (s); 0.96 (s); 0.99 (s); 1.00 (s); 1.04 (2s); 1.08 (2s); 1.115 (d, J=7 Hz); 1.12 (d, J=7 Hz): total 16.5 H.

MS (m/e): 220 (M+), 205, 191, 177, 163, 149, 135, 121, 105, 91,

Odour: musk-like, woody, pine needle-like.

Where desired, an isomer separation can now be carried out, e.g. by preparative gas chromatography.

EXAMPLE 2

5-Nitro-1,1,2,3,3,6-hexamethylindane (65.0 g) is suspended in 580 ml of ethanol and treated with 6.5 g of 5% palladium on charcoal. The air is, after evacuation, replaced by nitrogen and this is thereupon replaced by hydrogen. The mixture is thereupon hydrogenated while cooling slightly with water at an internal temperature of 22°–27° C. After 24 hours 57.9 ml of about 36% aqueous formaldehyde solution are sprayed in. The hydrogenation is continued without interruption. 1.79 Equivalents of $H_2$ are taken up within 24 hours. Thereafter, the catalyst is filtered off under suction. The ethanol is distilled off for the most part, the residue is taken up in tert.butyl methyl ether and washed with water.

The aqueous phases are extracted twice with tert.butyl methyl ether and, after drying over $MgSO_4$, the combined organic phases are concentrated. After drying in a high vacuum there remain 62.5 g of 5-dimethylamino-1,1,2,3,3,6-hexamethylindane which are processed directly. 5-Dimethylamino-1,1,2,3,3,6-hexamethylindane (125.85 g) is dissolved in 210 ml of tetrahydrofuran and 630 ml of ethylenediamine and treated with 152.9 ml of diethylene glycol monoethyl ether. The mixture is now cooled to a temperature of +5° C. using an isopropanol/dry-ice bath and treated while stirring within 5 minutes with 7.12 g of lithium wire in pieces 2–3 cm in length. After 30 minutes there are added rapidly at an internal temperature of 20° C. 152.9 ml of diethylene glycol monoethyl ether and 7.12 g of lithium wire. After about 1 hour the reaction mixture is poured on to 0.6 l of tert.butyl methyl ether and ice. The organic phase is thereupon washed neutral with water and the aqueous phases are extracted with tert.butyl methyl ether. The combined organic phases are treated with 170 ml of water and 104.5 g of 65% sulphuric acid while cooling slightly. The mixture is stirred vigorously at room temperature for 18 hours. The aqueous phase is separated and the organic phase is shaken twice with 20% $H_2SO_4$. Thereupon it is washed neutral with water, with 4% soda solution and with water.

The aqueous phases are extracted with tert.butyl methyl ether and the combined organic phases are dried over $MgSO_4$ and concentrated on a rotary evaporator. There remain 95.05 g of an oil which are distilled over a 15 cm Widmer column. The fractions having the boiling point 81°–87° C./0.04 mbar (77.45 g. $n_D^{20}$ 1.4875) are the so-called olfactory quality of 1,1,2,3,3,6-hexamethyl-4,5,6,7-tetrahydro-5-indanone. This has a musk-like, slightly woody, fruity and pine needle-like odour.

EXAMPLE 3

Flowery Composition (in the Direction of Lily of the Valley-Jasmine)

| Cedarwood distilled | 50.00 |
|---|---|
| Benzyl acetate extra | 80.00 |
| Geraniol extra | 50.00 |
| Isoraldeine 95 ® Givaudan (alpha-isomethylionone) | 30.00 |
| Phenylethyl alcohol | 120.00 |
| Hydroxycitronellal | 120.00 |
| Benzyl salicylate | 70.00 |
| Methyl Dihydrojasmonate | 150.00 |
| α-Hexylcinnamaldehyde | 200.00 |
| Cetonial ™ (Givaudan) (2-methyl-3-[3',4'-methylenedioxybenzene]-propionaldehyde) | 15.00 |
| cis-3-Hexenyl salicylate | 15.00 |
| Evernyl ® (Roure S.A.) (methyl 2,4-dihydroxy-3,5-dimethylbenzoate) | 5.00 |
| Clove bud oil | 8.00 |
| Heliotropin | 8.00 |
| Mandarin oil | 15.00 |
| Phenylacetaldehyde 85% in phenylethyl alcohol | 2.00 |
| Undecylaldehyde 1% in Carbitol | 2.00 |

| | |
|---|---|
| -continued | |
| Dipropylene glycol | 60.00 |

The addition of 6% of 1,1,2,3,3,6-hexamethyl-4,5,6,7-tetrahydro-5-indanone confers a powerful radiance and a velvety softness to this composition. Moreover, the on the whole natural and cosmetic impression of this composition is underlined in an extraordinary manner.

We claim:
1. 1,1,2,3,3,6-Hexamethyl-4,5,6,7-tetrahydro-5-indanone.
2. An odorant composition which comprises 1,1,2,3,3,6-hexamethyl-4,5,6,7-tetrahydro-5-indanone and at least one other olfactive agent.

* * * * *